United States Patent [19]

Moore, Jr.

[11] 4,132,729

[45] Jan. 2, 1979

[54] PURIFICATION OF 2-AMINO-2,4-DIMETHYL-4-METHOXY PENTANENITRILE

[75] Inventor: Earl P. Moore, Jr., Hockessin, Del.

[73] Assignee: E. I. Du Pont de Nemours and Company, Wilmington, Del.

[21] Appl. No.: 851,389

[22] Filed: Nov. 14, 1977

[51] Int. Cl.$^2$ .................. C07C 120/00; C07C 121/43
[52] U.S. Cl. ............... 260/465.5 R; 260/192
[58] Field of Search .............. 260/465.5 R, 192

[56] References Cited

U.S. PATENT DOCUMENTS

| 3,541,132 | 11/1970 | Knowles | 260/465.5 R |
| 4,028,345 | 6/1977 | Moore, Jr. | 260/192 |

*Primary Examiner*—Joseph Paul Brust

[57] ABSTRACT

Process for removing water from a solution of water in 2-amino-2,4-dimethyl-4-methoxy pentanenitrile comprising treating said pentanenitrile solution with sufficient ammonia to form an ammonia concentration in the ammonia-water composition of at least 18% by weight at from 0° to 50° C, to cause an aqueous layer and a pentanenitrile layer to form, separating the pentanenitrile layer and the aqueous layer and then optionally removing ammonia from the pentanenitrile layer and optionally reacting the pentanenitrile with substantially no ammonia in the presence of a metal hypochlorite and a surfactant to prepare 2,2'-azobis(2,4-dimethyl-4-methoxy pentanenitrile).

6 Claims, No Drawings

PURIFICATION OF 2-AMINO-2,4-DIMETHYL-4-METHOXY PENTANENITRILE

BACKGROUND OF THE INVENTION

1. Field of Use

The present invention relates to a process for removing water from a solution of water in 2-amino-2,4-dimethyl-4-methoxy pentanenitrile. More specifically, the present invention relates to a process for removing water from a solution of water in 2-amino-2,4-dimethyl-4-methoxy pentanenitrile by treating said pentanenitrile solution with sufficient ammonia to form an ammonia concentration in the ammonia-water composition of at least 18% by weight to form an aqueous layer and a pentanenitrile layer and separating the aqueous layer from the pentanenitrile layer.

2. Prior Art

U.S. Pat. No. 3,541,132 discloses the preparation of aminonitriles, e.g., 2-amino-2,4-dimethyl-4methoxy pentanenitrile by the reaction of a ketone with hydrogen cyanide and ammonia. The procedure disclosed results in the preparation of a solution of water in pentanenitrile, ammonia and impurities present in the water. Such pentanenitrile solutions when used to prepare the corresponding azonitrile compound by the process disclosed in U.S. Pat. No. 4,028,345 results in the preparation of an azonitrile compound with dark-colored impurities and reduced yields of said azonitrile compound. The removal of this water and impurities from the pentanenitrile has heretofore been commercially impractical.

Additionally, the removal in the presence of water of residual ammonia is difficult and time consuming. The presence of ammonia in the pentanenitrile can adversely affect its use in the process for the preparation of an azonitrile compound wherein a metal hypochlorite is used.

SUMMARY OF THE INVENTION

The present invention is directed to a process comprising treating a solution of water in 2-amino-2,4-dimethyl-4-methoxy pentanenitrile with sufficient ammonia to form an ammonia concentration in the water-ammonia composition of at least 18% by weight at from 0° to 50° C. to cause an aqueous layer and a pentanenitrile layer to form and separating the pentanenitrile layer and the aqueous layer. Thus, according to the process of the present invention, 2-amino-2,4-dimethyl-4-methoxy pentanenitrile can be prepared with reduced amounts of water. The pentanenitrile layer can then be further purified by the removal of residual ammonia.

Treatment of the pentanenitrile with ammonia to remove water according to the process of this invention permits the subsequent removal of the ammonia in less time than when ammonia removal is conducted before water removal.

It has been found that when a solution of water in 2-amino-2,4-dimethyl-4-methoxy pentanenitrile is treated with ammonia to remove the water and the pentanenitrile is then used to prepare the corresponding azonitrile by reaction with a metal hypochlorite in the presence of a surfactant according to the process disclosed in U.S. Pat. No. 4,028,345, the corresponding azonitrile compound produced possesses less color than when the process of the present invention is not used. Additionally, in said preparation of the azonitrile compound filtration time for the final separation of the azonitrile is reduced when the water is removed from the pentanenitrile prior to the reaction to form the azonitrile.

Thus the process of the present invention results in the removal of the water present in said pentanenitrile solution that cannot easily be separated because of its solubility in the pentanenitrile and the concomitant removal of the impurities dissolved in said water. Accordingly, the process of this invention also involves the further purification of the pentanenitrile after water removal. This further purification involves the removal of residual ammonia from the pentanenitrile after water removal. A further embodiment of the invention is the additional step of reacting the pentanenitrile after water and ammonia removal with a metal hypochlorite in the presence of a surfactant according to the process described in U.S. Pat. No. 4,028,345 to prepare the corresponding azonitrile.

Thus the present invention can in a narrower manner be described as an improvement in the process of U.S. Pat. No. 4,028,345. More specifically, the present invention may also be described as an improvement in the process of reacting an aminonitrile with a metal hypochlorite in the presence of a surfactant, said improvement comprising treating a solution of water in 2-amino-2,4-dimethyl-4-methoxy pentanenitrile with sufficient ammonia to form a concentration of ammonia in the water-ammonia composition of at least 18% by weight to cause the formation of an aqueous layer and a pentanenitrile layer, separating the aqueous layer and the pentanenitrile layer and removing residual ammonia from the pentanenitrile layer before reaction with the metal hypochlorite to form the corresponding azonitrile.

The use of said pentanenitrile solution, without treatment by the process of this invention to prepare the corresponding azonitrile, results in an axonitrile with greater color as measured by APHA tests. When the pentanenitrile solution is treated according to the present process, and is used to prepare an azonitrile compound by reactions described herein, the color and the rate of filtration of the azonitrile from the reaction medium involved are both improved. This is, color is reduced and rate of filtration is increased over that obtained when water is not removed from the pentanenitrile solution.

In the reaction of the pentanenitrile to form the corresponding azonitrile, the presence of ammonia adversely affects the reaction. Metal hypochlorite can react with ammonia that is present to form undesirable chloroamines which can be toxic and explosive. Also, the presence of ammonia severely reduces the yield of azonitrile because of its reactivity with the hypochlorite. This reactivity results in the depletion of the hypochlorite which upsets the balance of hypochlorite and aminonitrile required in the azonitrile preparation. Therefore, the removal of ammonia is essential before reacting the pentanenitrile to form the azonitrile. The pentanenitrile solutions of this invention, if water is first removed therefrom, can be purged of residual ammonia much more rapidly than when the water is not removed.

DESCRIPTION OF THE INVENTION

The process described in U.S. Pat. No. 3,541,132 for the preparation of aminonitriles results in the formation of a reaction product comprising the aminonitrile, ammonia, water and impurities.

The 2-amino-2,4-dimethyl-4-methoxy pentanenitrile that is formed with the reaction of 4-methyl-4-methoxy-2-pentanone, ammonia and HCN according to U.S. Pat. No. 3,541,132, unlike the other aminonitriles that are thus prepared, is miscible with water and thus is prepared as a homogeneous liquid mixture containing water. One mole of the ketone reacts with one mole of hydrogen cyanide and one mole of ammonia to form one mole of aminonitrile and one mole of water. Thus, the reaction product, when the pentanenitrile is prepared, comprises a solution of water in the pentanenitrile. The water present when other aminonitriles are prepared is mostly present in a separate aqueous phase and is removed usually by decantation. Subsequent ammonia removal is relatively easily achieved. Due to said miscibility, the water levels normally present in said pentanenitrile cannot be easily reduced to acceptable levels. The process of the present invention results in removal of 80% or more of the water present in said pentanenitrile solution. Additionally, ammonia cannot be relatively easily removed from the pentanenitrile solution because of the presence of water. Surprisingly, it has been found that removal of substantially all of the water present in the pentanenitrile solution is achieved by the addition of ammonia sufficient to form a concentration of ammonia in the water-ammonia composition that results in at least 18% by weight and subsequent separation of the two phases that result. Remaining ammonia can easily be removed from the pentanenitrile after the water is removed. Generally the ammonia is removed from the pentanenitrile by degassing operations, e.g., by drawing a vacuum over the pentanenitrile or by passing air or nitrogen through the pentanenitrile layer.

In the process of the present invention, the ammonia present after the water has been removed can quickly be reduced to levels of 0.2% by weight based on the pentanenitrile which thereby minimizes the above adverse effects of the ammonia. Thus, in the process of this invention, the removal of the ammonia means the reduction of ammonia to 0.2% by weight or less based on the aminonitrile.

What is meant by the removal of water or the removal of substantially all of the water in the pentanenitrile solution is the removal of 80% or more of said water.

Generally a concentration of at least 18% by weight of ammonia based on the water-ammonia composition that results from the water-pentanenitrile solution and ammonia is required to permit the removal of said water. Thus, the amount of ammonia required must be sufficient to form a water-ammonia composition having a concentration of ammonia of at least 18% by weight. Sufficient ammonia will not be present in the water at levels below 18% to achieve the desired separation. Thus, to remove the maximum amount of water, at least 18% by weight of ammonia is required. Preferably the amount of ammonia is 18% to 31% by weight based on the resulting water-ammonia composition.

The ammonia added may be in the form of ammonia gas or an aqueous ammonia solution. However, concentrations of ammonia in the upper concentration range of this invention may not be attainable with the addition of aqueous ammonia in view of the availability of such solution of up to 30% by weight of ammonia.

The present invention can be carried out generally at a temperature of 0° to 50° C. The process of the present invention is operable at temperatures below 0° C., but because the point at which water will freeze under these conditions is approached, it is not desirable to operate at temperatures below 0° C. At temperatures above 50° C., the pentanenitrile will decompose at rather rapid rates. It is therefore preferred that the process of this invention be carried out at a temperature of 0° to 40° C.

The process of the present invention is conveniently carried out at atmospheric pressure. Other pressures can be used but there is no need to operate at these other pressures.

Water separates from the pentanenitrile when the concentration of ammonia in the aqueous ammonia solution is at least 18% by weight. Cooling of the resulting ammonia-water-pentanenitrile mixture facilitates the phase separation of water and pentanenitrile. However, cooling is not mandatory. Likewise, external addition of ammonia may not required to attain the level of at least 18% described herein. In the preparation of the pentanenitrile by the process disclosed in U.S. Pat. No. 3,541,132, which is hereby incorporated by reference, steps, e.g., cooling, can be taken to prevent the loss of unreacted ammonia after the pentanenitrile preparation is complete and is discharged from the reactor. Thus, by preventing the loss of ammonia that normally occurs when the pentanenitrile product is discharged, the external addition of ammonia may not be required or lesser amounts will have to be added. Normally, the aminonitrile reaction product of U.S. Pat. No. 3,541,132 is warmed in order to facilitate the venting of the residual ammonia to a level which enables the aminonitrile product to be subsequently handled without undesirable evolution of ammonia and foaming. Therefore, it is generally necessary to add ammonia to the pentanenitrile solution according the process of this invention.

In the process of this invention the ammonia treatment results in the formation of two phases. The aqueous phase and the pentanenitrile phase are separated generally by removing the aqueous phase from the pentanenitrile phase and then air or nitrogen is passed through the pentanenitrile phase to remove the ammonia that remains in said pentanenitrile. This removal of the ammonia after water removal can be accomplished in half the time required when the water is not removed.

The azonitrile preparation from the aminonitrile is further described in U.S. Pat. No. 4,028,345, which is hereby incorporated by reference, involving the preparation of azonitriles by reacting aminonitriles, e.g., the pentanenitrile of this invention, in the presence of a metal hypochlorite, water and a surfactant.

The APHA color measurement procedure used in evaluating this invention is disclosed in *Standard Methods for Examination of Water and Wastewater,* 14th Edition, 1975, Procedure 204A.

2-Amino-2,4-dimethyl-4-methoxy pentanenitrile of this invention is useful in the preparation of the corresponding azonitrile compound which is useful as an initiator in polymerization reactions.

The present invention is further illustrated by the examples that follow wherein all percentages are by weight unless otherwise indicated.

EXAMPLE 1

Preparation of Pentanenitrile

Five hundred twenty-eight grams of 4-methoxy-4-methyl-2-pentanone (99% purity) were charged to a one-liter pressure reactor and cooled to 10° C. Five grams of ammonia were added and the mixture was stirred as 108.5 g hydrogen cyanide were added in 15 minutes maintaining the temperature at 10° C. Ammonia was then pressured into the reactor at 50 psi for 30 minutes allowing temperature to increase to 40° C. The ammonia pressure then was increased to 70 psi and maintained at this level for 7½ hours. The reactor then was vented of ammonia slowly with warming to attain an internal pressure of 1 atmosphere. The crude reaction product was discharged and divided into 3 equal portions.

Treatment of Pentanenitrile with Ammonia

One portion of the crude reaction product from above was saturated with gaseous ammonia at 28° C. A dark-colored upper aqueous layer separated in about 30 minutes and was discarded leaving a pale orange-colored product as lower layer. It was estimated that more than 80% of the water present in the pentanenitrile before ammonia treatment was removed. Analysis showed that the aqueous phase contained 30% $NH_3$ at 28° C.

A second portion of the crude reaction product was cooled to 0° C. and $NH_3$ was introduced until the product became cloudy. The aqueous layer which was separated contained 18% $NH_3$ at 0° C. The reduction in water content in the lower pentanenitrile layer was estimated to be at least 80%.

The third portion of the crude reaction product was not treated.

Purging Pentanenitrile of Ammonia

Prior to reacting 2-amino-2,4-dimethyl-4-methoxy pentanenitrile with sodium hypochlorite to produce 2,2'-azobis(2,4-dimethyl-4-methoxy pentanenitrile), it is necessary to remove $NH_3$ to a level of about 0.2% or less, otherwise the $NH_3$ will react with the hypochlorite to form undesirable toxic chloramines at an unacceptably high level.

The three portions of pentanenitrile above were purged of $NH_3$ using a sintered glass porous tube and an air flow rate of 1,500 cc/min at a temperature of 40° C. Analysis for $NH_3$ content revealed that the two pentanenitrile samples from which the water had been removed lost $NH_3$ at twice the rate of the sample which had not been treated according to the teaching of this invention. In 30 minutes, the $NH_3$ in the water-free pentanenitrile was reduced to less than 0.2% by weight based on the pentanenitrile while more than 1 hour was required to accomplish this with the untreated material.

EXAMPLE 2

Preparation of Azonitriles

A. Treated Pentanenitrile

Forty-five grams of 2-amino-2,4-dimethyl-4-methoxy pentanenitrile of 87.0% purity after treatment with $NH_3$ at 28° C., separated from the resulting layer of 30% $NH_3$ in water and purged of remaining $NH_3$, were added in 30 minutes to a stirred solution of 311 g 9% NaOCl, 0.9 g dioctyldimethylammonium chloride and 0.52 g NaBr cooled at −5° C. The mixture was stirred for 30 minutes at −5° C. to complete the reaction and then treated with 5.0 g $SO_2$ and sufficient acid (HCl) to give a pH of 3.0 and stirred for 15 minutes at 10° C. The pH was finally adjusted to 11.0.

The product slurry was filtered through 11.0 cm Whatman 41 paper and the cake was washed with 800 ml water under 4 inches Hg vacuum. Filter time was 1 minute, 10 seconds, wash time was 2 minutes, 50 seconds.

The dried azonitrile weighed 37.4 g, a 96.8% yield, and had an APHA color (2% in dimethyl formamide) of 10.

This procedure is repeated using the same pentanenitrile after treatment with $NH_3$ at 0° C. to form an aqueous layer of 18% $NH_3$ in water, followed by separation of the resulting aqueous layer and purging of the pentanenitrile of residual $NH_3$. The azonitrile product filter time is approximately 1 minute, 15 seconds and wash time is approximately 2 minutes, 45 seconds. A product with an APHA color of 10 is obtained in approximately 96% yield.

B. Untreated Pentanenitrile

Forty-five grams of 2-amino-2,4-dimethyl-4-methoxy pentanenitrile with ammonia removed by purging of 84.2% purity were added in 30 minutes to a stirred mixture of 193.6 g 14.0% NaOCl, 107.5 g water, 0.9 g dioctyldimethylammonium chloride and 0.52 g NaBr cooled at −5° C. After 30 minutes, additional stirring at −5° C., 5.0 g $SO_2$ were introduced and concentrated hydrochloric acid was added to give pH 3.0 with stirring at 10° C. A final pH adjustment to 11.0 was made.

The product slurry was filtered through 11.0 cm Whatman 41 paper in 1 minute, 40 seconds and was washed with 800 ml water in 4 minutes, 20 seconds, a 50% slower total time than obtained above with treated pentanenitrile.

The dried azonitrile weighed 34.8 g, a 93.1% yield, and had an APHA color between 15 to 20.

While the invention has been described in considerable detail in the foregoing, it is to be understood that such detail is solely for the purpose of illustration and that variations can be made by those skilled in the art without departing from the spirit and scope of the invention except as set forth in the claims.

What is claimed is:

1. A process for removing water from a solution of water and 2-amino-2,4-dimethyl-4-methoxy pentanenitrile comprising treating said solution of water in 2-amino-2,4-dimethyl-4-methoxy pentanenitrile with sufficient ammonia to form a concentration of ammonia in the water-ammonia composition of at least 18% by weight of ammonia at a temperature of from 0° to 50° C. to form an aqueous layer and a pentanenitrile layer, and separating the pentanenitrile layer and the aqueous layer.

2. The process of claim 1 wherein the ammonia concentration in the ammonia-water composition is 18% to 31% by weight of ammonia.

3. The process of claim 1 wherein the temperature is from 0° to 40° C.

4. The process of claim 1 wherein the pentanenitrile layer after separation is further modified by removing ammonia.

5. The process of claim 4 wherein the ammonia concentration in the ammonia-water composition is 18% to 31% by weight of ammonia.

6. The process of claim 4 wherein the temperature is from 0° to 40° C.

* * * * *

UNITED STATES PATENT OFFICE
CERTIFICATE OF CORRECTION

PATENT NO. : 4,132,729
DATED : JANUARY 2, 1979
INVENTOR(S) : EARL P. MOORE, JR.

It is certified that error appears in the above-identified patent and that said Letters Patent are hereby corrected as shown below:

Column 6, line 58, Claim 4, "modified" should be -- purified --.

Signed and Sealed this

Nineteenth Day of June 1979

[SEAL]

Attest:

RUTH C. MASON
*Attesting Officer*

DONALD W. BANNER
*Commissioner of Patents and Trademarks*